(12) United States Patent
Keller et al.

(10) Patent No.: US 10,817,049 B1
(45) Date of Patent: Oct. 27, 2020

(54) KINESTHETIC SENSORS FOR DETERMINING ANGULAR DISPLACEMENTS

(71) Applicant: Facebook Technologies, LLC, Menlo Park, CA (US)

(72) Inventors: Sean Jason Keller, Bellevue, WA (US); Tristan Thomas Trutna, Seattle, WA (US); David R. Perek, Seattle, WA (US); Bruce A. Cleary, III, Bothell, WA (US); Brian Michael Scally, Seattle, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/414,766

(22) Filed: May 16, 2019

Related U.S. Application Data

(63) Continuation of application No. 15/380,127, filed on Dec. 15, 2016, now Pat. No. 10,331,206.

(60) Provisional application No. 62/267,834, filed on Dec. 15, 2015.

(51) Int. Cl.
*G06F 3/01* (2006.01)
*A61B 5/00* (2006.01)
*A61B 5/11* (2006.01)
*G06T 19/00* (2011.01)

(52) U.S. Cl.
CPC ............ *G06F 3/011* (2013.01); *A61B 5/1114* (2013.01); *A61B 5/1121* (2013.01); *A61B 5/6826* (2013.01); *G06T 19/006* (2013.01); *A61B 2562/168* (2013.01)

(58) Field of Classification Search
None
See application file for complete search history.

(56) References Cited

U.S. PATENT DOCUMENTS

| 4,574,615 | A | 3/1986 | Bower et al. |
| 2004/0253183 | A1 | 12/2004 | Uber et al. |
| 2006/0015191 | A1* | 1/2006 | Bergamasco ........ A61B 5/1071 623/24 |
| 2010/0060389 | A1 | 3/2010 | Schneider et al. |
| 2015/0086424 | A1 | 3/2015 | Putnam et al. |
| 2015/0087559 | A1 | 3/2015 | Putnam et al. |
| 2017/0090666 | A1* | 3/2017 | Pahud ................. G06F 3/04842 |

* cited by examiner

*Primary Examiner* — Joseph R Haley
(74) *Attorney, Agent, or Firm* — Fenwick & West LLP (57) ABSTRACT

A kinesthetic sensor measure angular displacement of body parts of users by measuring a density of substances contained in a conduit of the kinesthetic sensor. For example, the kinesthetic sensor measures the density of substance including in a conduit by transmitting a signal into the conduit and measuring the signal after the signal passes through the conduit and one or more substances included in the conduit. Based on the density of the one or more substances included in the conduit from the measured signal, an angular displacement of a user's body part proximate to the kinesthetic sensor is determined. Kinesthetic sensors may use different architectures such as an open-loop, a closed-loop architecture, or an architecture using blood vessels as conduits. Additionally, kinesthetic sensors can be flexible to conform to physical contours of different body parts.

20 Claims, 4 Drawing Sheets

KINESTHETIC SENSORS FOR DETERMINING ANGULAR DISPLACEMENTS

CROSS-REFERENCE TO RELATED APPLICATION

This application is a continuation of co-pending U.S. patent application Ser. No. 15/380,127, filed Dec. 15, 2016, which claims the benefit of U.S. Provisional Patent Application Ser. No. 62/267,834, titled "Kinesthetic Sensors for Determining Angular Displacements," filed on Dec. 15, 2015, which is incorporated by reference herein in its entirety.

BACKGROUND

The present disclosure generally relates to systems for providing virtual reality experiences to users, and specifically to a kinesthetic sensor for determining angular displacements of portions of a user.

Virtual reality systems, which may also include augmented reality (AR) systems, create a virtual (or augmented) reality environment that provides sensory experiences such as sight, hearing, touch, and smell and allow multimodal and real-time interaction between a user and the virtual (or augmented) reality environment. In such systems it is desirable to have peripheral devices (e.g., a glove worn by the user) that a user may use to interact with the virtual (or augmented) environment. Such peripheral devices include sensors capable of detecting movements of the user. However, these peripheral sensors are often relatively complex, bulky, and/or are incapable of detecting fine movements of the user (e.g., slight bend in a finger).

SUMMARY

Embodiments relate to kinesthetic sensors for measuring angular displacement of body parts (e.g., a finger joint) of users. A kinesthetic sensor is flexible, which allows it to conform to the physical contour of a user's body part. The kinesthetic sensor monitors changes in density of a substance and outputs a signal based on the changes in the density of the substance that can be used to determine an angular displacement of the user's body part. The substance may be included in the sensor or external to the sensor.

Some kinesthetic sensors use an open-loop architecture. In the open-loop architecture, a kinesthetic sensor includes a tube containing a first fluid and periodically injects a fixed volume of a second fluid (e.g., a gas) into the first fluid, forming a stream of bubbles in the first liquid. The second fluid does not mix with the first fluid and is separate from the first fluid. The first and second fluid may be, for instance, ambient air, some other type of gas, oil, waxes, or silicone. If there is no angular displacement in the tube, the spacing between the bubbles formed from injection of the second fluid is constant. The bubbles propagate through the tube and are emitted into the atmosphere. The bubbles can also be collected for reuse or disposal. At one or more monitoring regions, the kinesthetic sensor has sensors (e.g., ultrasound sensors) that monitor changes in density of the first fluid and the second fluid in the monitoring regions. The sensors determine a density profile describing changes in density over time for a particular region (e.g., monitoring region) of the kinesthetic sensor. Angular displacement of the tube (i.e., a bend in the tube) of the kinesthetic sensor is correlated with changes in the density profile. Hence, the kinesthetic sensor monitors changes in the density profile at the one or more monitoring regions using the one or more sensors (e.g., ultrasound sensors) to determine an amount of angular displacement of the tube. As the tube conforms to a body part of the user, the determined amount of angular displacement for the tube can also be attributed to the body part of the user to which the tube conforms, allowing determination of the angular displacement of the body part.

In various embodiments, the kinesthetic sensor may be implemented using architectures different from the previously described open-loop (or partially open-loop) architecture where gas is injected into a tube, propagates through the tube, and then exits the tube either venting to the atmosphere or being collected. For example, an alternative kinesthetic sensor includes a closed-loop pipe containing foams of varying density. The foam inside the pipe re-circulates and does not exit the pipe. In another embodiment, a kinesthetic sensor measures the propagation of blood pulses (i.e., changes in density that occur in a blood vessel) of a user's body part proximate to the kinesthetic sensor to measure the physical contour of the user's body part. In this embodiment, a blood vessel of the user's body part proximate to the kinesthetic sensor acts as a "tube" or "pipe" of the kinesthetic sensor.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

System Overview

Figure 1:
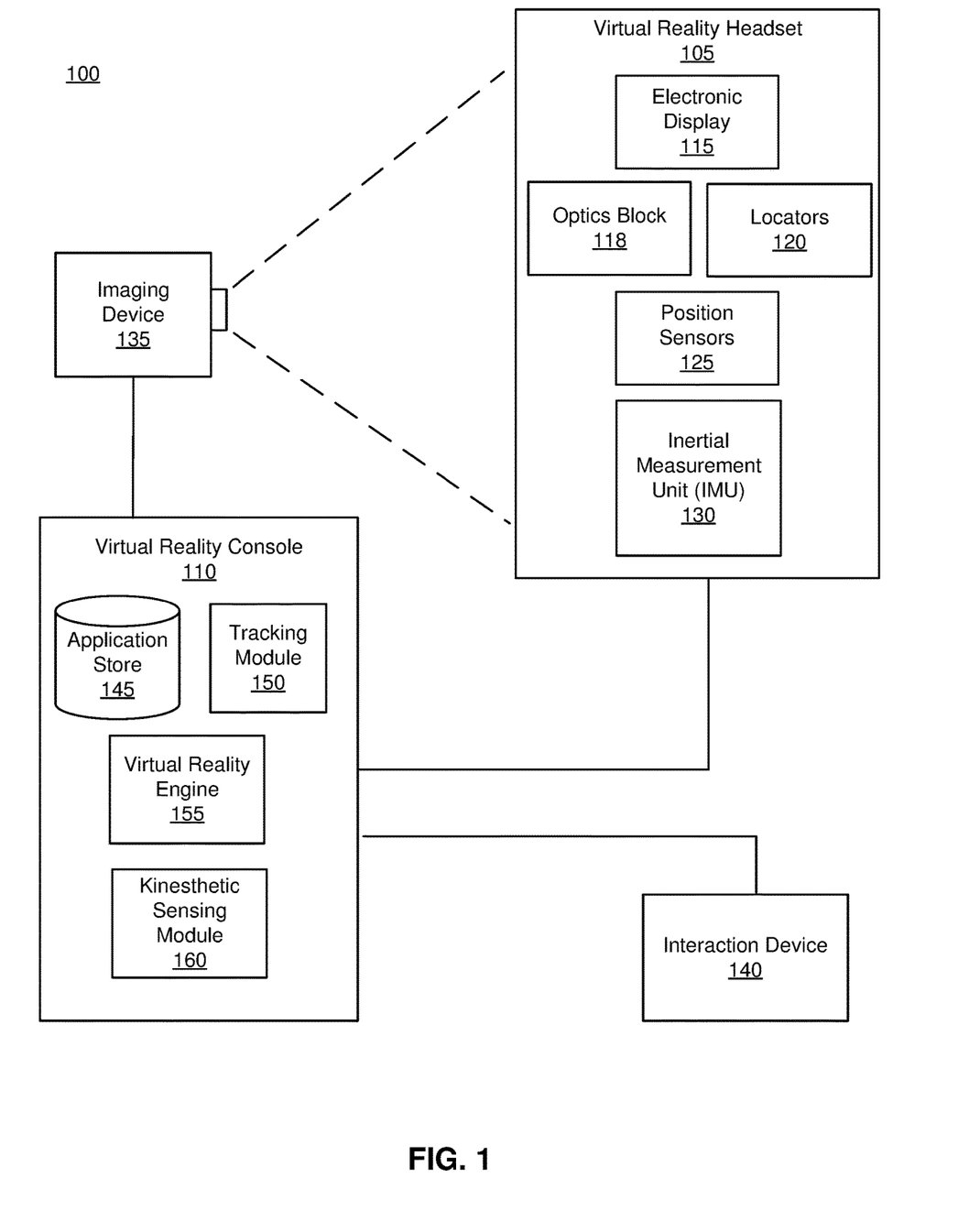
FIG. 1 is a block diagram of a system environment including a virtual reality system, in accordance with an embodiment.

FIG. 1 is a block diagram of a virtual reality (VR) system environment 100 in which a VR console 110 operates. Although FIG. 1 shows a VR system environment 100 for purposes of illustration, in other embodiments, the following disclosure may be adapted for use in an augmented reality (AR) system environment where a headset combines virtual content with images or video of an environment external to the headset or in any other system environment using a head mounted display (HMD) to present content. The system environment 100 shown by FIG. 1 comprises a VR headset 105, an imaging device 135, a virtual reality console 110, and an interaction device 140. While FIG. 1 shows an example system 100 including one VR headset 105, one imaging device 135, and one interaction device 140, in other embodiments any number of these components may be included in the system 100. For example, there may be multiple VR headsets 105 each having an associated interaction device 140 and being monitored by one or more imaging devices 135, with each VR headset 105, interaction device 140, and imaging devices 135 communicating with the VR console 110. In alternative configurations, different and/or additional components may be included in the system environment 100. Similarly, the functions can be distributed among the components in a different manner than is described here. For example, some or all of the functionality of the VR console 110 may be contained within the VR headset 105.

The VR headset 105 is a head-mounted display that presents content to a user. Examples of content presented by the VR head set include one or more images, video, audio, or any combination thereof. In some embodiments, audio is presented via an external device (e.g., speakers and/or headphones) that receives audio information from the VR headset 105, the VR console 110, or both, and presents audio data based on the audio information. In some embodiments, the VR headset 105 may also act as an augmented reality (AR) headset. In these embodiments, the VR headset 105 augments views of a physical, real-world environment with computer-generated elements (e.g., images, video, sound, etc.).

The VR headset 105 includes an electronic display 115, an optics block 118, one or more locators 120, one or more position sensors 125, and an inertial measurement unit (IMU) 130. However, in other embodiments, the VR headset 105 may include different or additional components than the example shown in FIG. 1. Similarly, in various embodiments, the VR headset 105 may differently distribute the functionality further described below among components.

The electronic display 115 displays images to the user in accordance with data received from the VR console 110. In various embodiments, electronic display 115 may comprise a single electronic display or multiple electronic displays (e.g., a display for each eye of a user). Examples of electronic display 115 include: a liquid crystal display (LCD), an organic light emitting diode (OLED) display, an active-matrix organic light-emitting diode display (AMO-LED), some other display, or some combination thereof.

The optics block 118 magnifies received light from the electronic display 115, corrects optical errors associated with the image light, and directs the corrected image light to a user of the VR headset 105 for presentation. In various embodiments, the optics block 118 includes one or more optical elements. An optical element may be an aperture, a Fresnel lens, a convex lens, a concave lens, a filter, or any other suitable optical element that affects image light emitted from the electronic display 115. Moreover, the optics block 118 may include combinations of different optical elements. In some embodiments, one or more of the optical elements in the optics block 118 may have one or more coatings, such as anti-reflective coatings.

The locators 120 are objects located in specific positions on the VR headset 105 relative to one another and relative to a specific reference point on the VR headset 105. A locator 120 may be a light emitting diode (LED), a corner cube reflector, a reflective marker, a type of light source that contrasts with an environment in which the VR headset 105 operates, or some combination thereof. In embodiments where the locators 120 are active (i.e., an LED or other type of light emitting device), the locators 120 may emit light in the visible band (~380 nm to 750 nm), in the infrared (IR) band (~750 nm to 1 mm), in the ultraviolet band (10 nm to 380 nm), in some other portion of the electromagnetic spectrum, or in some combination thereof.

In some embodiments, the locators 120 are located beneath an outer surface of the VR headset 105, which is transparent to the wavelengths of light emitted by or reflected by the locators 120. The outer surface of the VR headset 105 may additionally or alternatively be thin enough not to substantially attenuate the wavelengths of light emitted by or reflected by the locators 120. Additionally, in some embodiments, the outer surface or other portions of the VR headset 105 are opaque in the visible band of wavelengths of light. Thus, the locators 120 may emit light in the IR band under an outer surface that is transparent in the IR band but opaque in the visible band.

The IMU 130 is an electronic device that generates fast calibration data based on measurement signals received from one or more of the position sensors 125. A position sensor 125 generates one or more measurement signals in response to motion of the VR headset 105. Examples of position sensors 125 include: one or more accelerometers, one or more gyroscopes, one or more magnetometers, another suitable type of sensor that detects motion, a type of sensor used for error correction of the IMU 130, or some combination thereof. The position sensors 125 may be located external to the IMU 130, internal to the IMU 130, or some combination thereof.

Based on the one or more measurement signals from one or more position sensors 125, the IMU 130 generates fast calibration data indicating an estimated position of the VR headset 105 relative to an initial position of the VR headset 105. For example, the position sensors 125 include multiple accelerometers to measure translational motion (forward/back, up/down, left/right) and multiple gyroscopes to measure rotational motion (e.g., pitch, yaw, roll). In some embodiments, the IMU 130 rapidly samples the measurement signals and calculates the estimated position of the VR headset 105 from the sampled data. For example, the IMU 130 integrates the measurement signals received from the accelerometers over time to estimate a velocity vector and integrates the velocity vector over time to determine an estimated position of a reference point on the VR headset 105. Alternatively, the IMU 130 provides the sampled measurement signals to the VR console 110, which determines the fast calibration data. The reference point is a point that may be used to describe the position of the VR headset 105. While the reference point may generally be defined as a point in space; however, in practice the reference point is defined as a point within the VR headset 105 (e.g., a center of the IMU 130).

The IMU 130 receives one or more calibration parameters from the VR console 110. As further discussed below, the one or more calibration parameters are used to maintain tracking of the VR headset 105. Based on a received calibration parameter, the IMU 130 may adjust one or more IMU parameters (e.g., sample rate). In some embodiments, certain calibration parameters cause the IMU 130 to update an initial position of the reference point so the initial position corresponds to a next calibrated position of the reference point. Updating the initial position of the reference point as the next calibrated position of the reference point helps reduce accumulated error associated with the determined estimated position. The accumulated error, also referred to as "drift error," causes the estimated position of the reference point to "drift" away from the actual position of the reference point over time.

The imaging device 135 generates slow calibration data in accordance with calibration parameters received from the VR console 110. Slow calibration data includes one or more images showing observed positions of the locators 120 that are detectable by the imaging device 135. The imaging device 135 may include one or more cameras, one or more video cameras, any other device capable of capturing images including one or more of the locators 120, or some combination thereof. Additionally, the imaging device 135 may include one or more filters (e.g., used to increase signal to noise ratio). The imaging device 135 is configured to detect light emitted by or reflected by locators 120 in a field of view of the imaging device 135. In embodiments where the locators 120 include passive elements (e.g., a retroreflector), the imaging device 135 may include a light source that illuminates some or all of the locators 120, which retro-reflect the light towards the light source in the imaging device 135. Slow calibration data is communicated from the imaging device 135 to the VR console 110, and the imaging device 135 receives one or more calibration parameters from the VR console 110 to adjust one or more imaging parameters (e.g., focal length, focus, frame rate, ISO, sensor temperature, shutter speed, aperture, etc.)

The interaction device 140 configured to be worn by a user (e.g., a glove, a elbow pad, a knee pad, or a garment) and enables the user to interact with the VR and/or AR environment presented by the VR headset 105. The interaction device 140 may be any suitable article contacting a portion of a user's body, in particular, one or more joints of the user's body. For example, the interaction device 140 is a glove worn by the user, a jacket, pants, another clothing article that is worn by the user, or some combination thereof. The interaction device 140 includes one or more kinesthetic sensors. A kinesthetic sensor measures angular displacement of a portion of the user's body proximate to the kinesthetic sensor. For example, a kinesthetic sensor placed over a finger joint provides information describing an angular displacement (bend) of the finger. The kinesthetic sensor provides the positional information describing this motion to the VR console 110. Kinesthetic sensors are described in detail below with respect to FIGS. 2 through 5. In some embodiments, based on the measured angular displacement, the interaction device 140 provides feedback such as an actuation (e.g., haptic feedback) that the user can sense.

The interaction device 140 allows a user to send action requests to the VR console 110. An action request is a request to perform a particular action. For example, an action request may be to start or to end an application or to perform a particular action within the application. An action request received by the interaction device 140 is communicated to the VR console 110, which performs an action corresponding to the action request. In some embodiments, one or more input devices (e.g., keyboard, joystick, etc.) may also be used to send action requests to the VR console 110. The interaction device 140 may include one or more IMUs, locators (similar to locators 120), and position sensors (similar to position sensors 125). The IMUs included on the interaction device 140 would provide fast calibration data to the VR console 110 indicating an estimated position of the interaction device 140 relative to an initial position of the interaction device 140, in a similar manner as described above with reference to IMU 130.

The VR console 110 provides content to the VR headset 105 for presentation to the user in accordance with information received from one or more of: the imaging device 135, the VR headset 105, and the interaction device 140. The VR console 110 may also instruct the interaction device 140 to provide feedback (e.g., haptic feedback). In the example shown in FIG. 1, the VR console 110 includes an application store 145, a tracking module 150, a virtual reality (VR) engine 155, and a kinesthetic sensing module 160. Some embodiments of the VR console 110 have different modules than those described in conjunction with FIG. 1. Similarly, the functions further described below may be distributed among components of the VR console 110 in different manners than described herein.

The application store 145 stores one or more applications for execution by the VR console 110. An application is a group of instructions that, when executed by a processor, generate content for presentation to the user. Content generated by an application may be in response to inputs received from the user via movement of the VR headset 105 or the interaction device 140. Examples of applications include: gaming applications, conferencing applications, video playback application, or other suitable applications.

The tracking module 150 calibrates the VR system environment 100 using one or more calibration parameters and may adjust one or more calibration parameters to reduce error in determination of the position of the VR headset 105 and/or the interaction device 140. For example, the tracking module 150 adjusts the focus of the imaging device 135 to obtain a more accurate position for observed locators on the VR headset 105 or on the interaction device 140. Moreover, calibration performed by the tracking module 150 also accounts for information received from the IMU 130. Additionally, if tracking of the VR headset 105 or the interaction device 140 is lost (e.g., the imaging device 135 loses line of sight of at least a threshold number of the locators 120), the tracking module 150 re-calibrates some or all of the VR system environment 100.

The tracking module 150 tracks movements of the VR headset 105 using slow calibration information from the imaging device 135. The tracking module 150 determines positions of a reference point of the VR headset 105 using observed locators 120 from the slow calibration information and a model of the VR headset 105. The tracking module 150 also determines positions of a reference point of the VR headset 105 using position information from the fast calibration information. Additionally, in some embodiments, the tracking module 150 may use portions of the fast calibration information, the slow calibration information, or some combination thereof, to predict a future location of the headset 105. The tracking module 150 provides the estimated or predicted future position of the VR headset 105 to the VR engine 155.

The tracking module 150 also tracks movements of the interaction device 140. The tracking module 150 may receive signals transmitted by one or more kinesthetic sensors of the interaction device 140 to determine geometric shapes of the kinesthetic sensors as well as of the interaction device 140. Similar to tracking the movements of the VR headset 105, the tracking module 150 may also use slow calibration information from the imaging device 135 to track movement of the interaction device 140. The tracking module 150 determines positions of a reference point of the interaction device 140 using observed locators 120 from the slow calibration information and a model of the interaction device 140. The tracking module 150 also determines positions of a reference point of the interaction device 140 using position information from the fast calibration information. Additionally, in some embodiments, the tracking module 150 may use portions of the fast calibration information, the slow calibration information, or some combination thereof, to predict a future location of the interaction device 140. The tracking module 150 provides the estimated or predicted future position of the interaction device 140 to the VR engine 155.

The VR engine 155 executes applications within the VR system environment 100 and receives position information, acceleration information, velocity information, predicted future positions, or some combination thereof of the VR headset 105 from the tracking module 150. Based on the received information, the VR engine 155 determines content to provide to the VR headset 105 for presentation to the user. For example, if the received information indicates that the user has looked to the left, the VR engine 155 generates content for the VR headset 105 that mirrors the user's movement in a virtual environment. Additionally, the VR engine 155 performs an action within an application executing on the VR console 110 in response to an action request received from the interaction device 140 and provides feedback to the user that the action was performed. One or more kinesthetic sensors of the interaction device 140 transmit signals comprising physical states (e.g., geometric shapes) of the interaction device 140 to the VR engine 155. Feedback provided to the user by the VR engine 155 may be based on the physical states of the interaction device 140. The provided feedback may be visual or audible feedback via the VR headset 105 or kinesthetic via the interaction device 140.

The kinesthetic sensing module 160 receives and processes signals (e.g., detection signals) from kinesthetic sensors to determine physical states (e.g., geometric shapes) of the interaction device 140. The kinesthetic sensing module 160 may calibrate a kinesthetic sensor when the kinesthetic sensor is initially used by a user or may calibrate the kinesthetic sensor regularly while it is used to minimize variance from different sizes of body parts of individual users, different motions (e.g., speed, amplitude, pattern, etc.), and different relative positions of the kinesthetic sensor. As such, the kinesthetic sensing module 160 can accurately detect the physical states of the kinesthetic sensor. For example, the kinesthetic sensing module 160 measures signals from a kinesthetic sensor when a user performs a predetermined motion to determine a correlation between detection signals output by the kinesthetic sensor and characteristics associated with the geometric shape of the kinesthetic sensor. The kinesthetic sensing module 160 may create a density profile of a kinesthetic sensor that describes changes in density within a conduit (e.g., an open-loop tube, a closed-loop pipe, or a blood vessel) of the kinesthetic sensor with times that are correlated with angular displacement of the conduit. For example, the density profile is a table including a detection signal, a corresponding density, a corresponding geometric shape, and a corresponding angular displacement from a reference state. Based on a detection signal received from a kinesthetic sensor, the kinesthetic sensing module 160 determines a corresponding angular displacement by looking up the received detection signal from the density profile. In various embodiments, the density profile further includes correlations of a detection signal with corresponding dimensions or numbers of gas bubbles within a region of the conduit of the kinesthetic sensor and with a corresponding absolute position of the region of the conduit of the kinesthetic sensor. By tracking the dimensions and/or quantity of gas bubbles within a predetermined region of the conduit of the kinesthetic sensor, the kinesthetic sensing module 160 may determine an absolute position of the kinesthetic sensor.

In various embodiments, the kinesthetic sensing module 160 may develop one or more machine learning models and use the developed machine learning models to correlate characteristics associated with a detection signal from a kinesthetic sensor and characteristics associated with an angular displacement of a corresponding body part proximate to the kinesthetic sensor. The machine learning models may include one or more logistic classifiers, decision trees, neural networks, deep learning models, or any combination thereof. The machine learning models are developed from training data provided to the kinesthetic sensing module 160. Hence, the kinesthetic sensing module 160 determines parameters of the machine learning models using the training data. The training data includes a set of geometric shapes of the conduit (or angular displacements of a particular joint) of a kinesthetic sensor labeled with signal characteristics. For example, the training data comprises geometric shapes or angular displacements of a kinesthetic sensor for which signal characteristics have previously been identified.

Example Interaction Device

Figure 2:
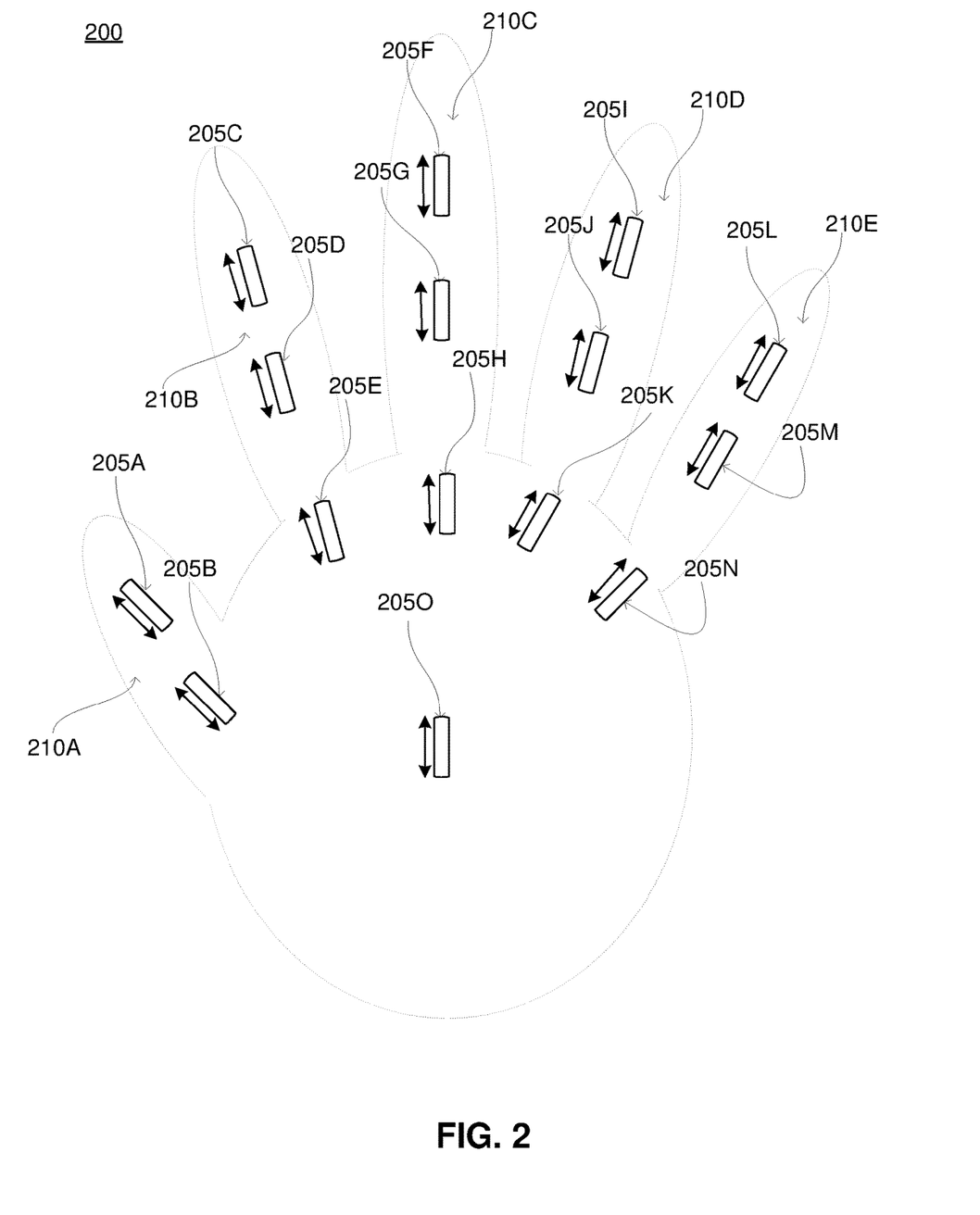
FIG. 2 is a diagram illustrating an interface including a plurality of kinesthetic sensors, in accordance with an embodiment.

FIG. 2 is a diagram illustrating an interaction device 200 including a plurality of kinesthetic sensors 205A-O (also referred to individually and collectively using reference number 205), according to an embodiment. In some embodiments, the interaction device 200 is a component of the VR system environment 100 (e.g., interaction device 140). In alternate embodiments, the interaction device 200 is part of another system in which angular displacement of a portion of a user is monitored. In the embodiment shown by FIG. 2. The interaction device 200 includes a plurality of kinesthetic sensors 205, which are each configured to measure angular displacement of various joints of a user's hand (or other body parts).

The kinesthetic sensors 205A-O are positioned at different locations on the glove. In the example shown by FIG. 2, each of the kinesthetic sensors 205A-N are positioned, respectively, at different finger joints along each finger 210A, 210B, 210C, 210D, 210E of the glove, while the kinesthetic sensor 205O is positioned in a central portion of the glove 200. The illustrated glove 200 shown in FIG. 2 is a left-handed glove where the kinesthetic sensors 205A-N contact a user's finger joints on the palmar portion (inside of the user's hand) of the user's hand and the kinesthetic sensor 205O contacts the palm of the user's hand. In other embodiments, one or more of the kinesthetic sensors 205A-N contact the user's finger joints on the posterior (back) portion of the hand. The sensors 205A-O may be positioned inside the glove 200 so they directly contact a user's skin when the user wears the glove 200. Alternatively, the sensors 205A-O may be positioned outside the glove 200 so they do not directly contact a user's skin when the user wears the glove 200. As further described below in conjunction with FIGS. 3A through 5, kinesthetic sensors 205 may include an open-loop sensor, a closed-loop sensor, or a tubeless sensor, and measure angular displacement of a user's body parts (e.g., joints), allowing the VR console 110 to provide the user with kinesthetic feedback based on positions of the user's body parts.

In various embodiments, a kinesthetic sensor 205 is flexible and configured to conform to a contour of a body part to measure an angular displacement of the body part (e.g., finger joint). When a user's body part moves (e.g., a finger curls, a thumb retracts, an arm lifts, a leg bends, etc.) and results in angular movement (e.g., flexion, extension, abduction, circumduction, lateral rotation, or medial rotation), a kinesthetic sensor 205 measures the angular displacement of the body part. That is, the kinesthetic sensor 205 measures a difference between an initial position and a final position of the user's body part with respect to an axis. The kinesthetic sensor 205 provides the angular displacement measurement to the VR console 110. Based on the angular displacement measurement, the VR console 110 generates kinesthetic feedback to the user, providing a more realistic virtual environment to the user. For example, when the user holds an object, the kinesthetic sensor 205 measures the angular displacement of the user's knuckles and based on the angular displacement, the VR console 110 provides the user with a perception of weight when the user picks up the object. As such, the content presented by the VR headset 105 is more realistic and more immersive.

Figure 3A:
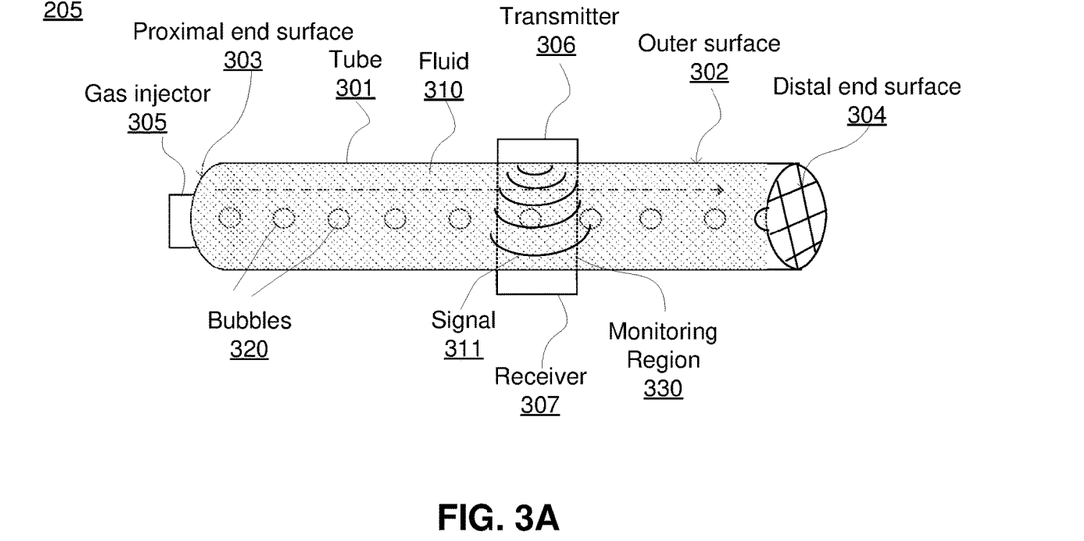
FIG. 3A illustrates an open-loop kinesthetic sensor in a straight state, in accordance with one embodiment.

FIG. 3A illustrates the kinesthetic sensor 205 in a straight state, according to an embodiment. The illustrated kinesthetic sensor 205 includes a tube 301, an injector 305, a transmitter 306, and a receiver 307. The tube 301 includes an outer surface 302, a proximal end surface 303, and a distal end surface 304. The outer surface 302 is made of flexible materials such as silicone, elastomer, and the like. When the kinesthetic sensor 205 is positioned contacting or proximate to a user's skin (e.g., in a glove worn by the user), the kinesthetic sensor 205 conforms to the contour of a user's body because of the flexibility of the outer surface 302. In some embodiments, an inner diameter of the tube 301 is between 0.5 and 4 millimeters (mms). The kinesthetic sensor 205 is in a straight state, which is shown in FIG. 3A, if there is no bend in the tube 301. If there is a bend in the tube 301, the kinesthetic sensor is in a bent state, which is further described below in conjunction with FIG. 3B.

The proximal end surface 303 is made of a material that may be the same as the material of the outer surface 302. The tube 301 contains a fluid 310 (e.g., water) between the proximal end surface 303 and the distal end surface 304. The material comprising the outer surface 302 and the proximal end surface 303 are not permeable to the fluid 310 or a bubble 320 within the fluid 310 (e.g., of injected air). Hence, the outer surface 320 and the proximal end surface 303 are made from one or more materials that do not permit the fluid 310 or the bubbles 320 to pass through. The distal end surface 304 may comprise a membrane made of a material different from the material of the outer surface 302. The membrane is made of a material that is not permeable to the fluid 310, but is permeable to the bubbles 320. Hence, the membrane is made of a material that does not permit the fluid 310 to pass through but permits the bubbles 320 to pass through.

The injector 305 is coupled to the proximal end surface 303 so the injector 305 injects a second fluid, which is different than the fluid 310, into the tube 301. For example, the second fluid is air or another type of gas having a different density than the fluid 310. The second fluid does not mix with the first fluid and is separate from the first fluid. Alternatively, the second fluid is a type of liquid having a different density than the fluid 310. For example, in some embodiments, the fluid 310 is water and the second fluid is ambient air. The fluid 310 and the second fluid can also be different types of oils, waxes, water, silicone, and the like. In some embodiments, the injector 305 is a Microelectromechanical system (MEMS). The injected second fluid may be at an ambient temperature or may be at a temperature different from the ambient temperature. The injector 305 injects discrete volumes of the second fluid into the tube 301 at a predetermined rate and dimension to generate the bubbles 320. The predetermined rate may be steady or variable. In some embodiments, a volume of the second fluid injected into the tube 301 is the same. However, in other embodiments, the injector 305 may vary the volume of second fluid injected into the tube 301 as the second fluid is injected (e.g., every third volume is larger than a most recently injected volume of the second fluid). A volume of the second fluid is illustrated as a bubble (e.g., one of the bubbles 320). Diameters of the bubbles 320 are smaller than an inner diameter of the tube 301.

In some embodiments, the kinesthetic sensor 205 may also include a micro-pump (not shown) that pumps volumes of ambient air into a small holding tank. For example, the micro-pump may be configured to compress ambient air into the small holding tank so compressed air in the tank is above a threshold pressure. The injector 305 may then inject fixed amounts of the compressed air into the fluid 310 in the tube 301.

The injector 305 may inject each volume of gas with an initial speed so the volumes of gas may traverse across the tube 301. Because the second fluid has a different density from the fluid 310, an inclination of the tube 301 causes the bubbles 320 to travel the inclination of the tube 301. In addition, a pressure difference across the tube 301 causes the fluid 310 to flow from a region of higher pressure to another region of lower pressure, causing the bubbles 320 to move.

The bubbles 320 are separated from each other by the fluid 310 contained in the tube 301. The bubbles 320 traverse the tube in a direction as shown by the dashed arrow in FIG. 3A from the proximal end surface 303 to the distal end surface 304, where the bubbles 320 dissipate through the distal end surface 304. The injector 305 injects the bubbles 320 at a steady rate, so when the tube 301 is in the straight state (e.g., no bend in the tube 301), the bubbles 320 are evenly distributed in the tube 301 where a particular bubble 320 is separated from an adjacent bubble 320 by a predetermined distance.

In some embodiments, a kinesthetic sensor 205 includes one or more transmitter 306 and receiver 307 pairs to measure one or more multiple local geometric shapes of the kinesthetic sensor 205. Each pair of a transmitter 306 and a receiver 307 measures a local geometric shape of the kinesthetic sensor 205 by measuring a density of the substances (e.g., the fluid 310 and the second fluid) within a monitoring region. The transmitter 306 is a device configured to emit a signal 311. For example, the transmitter 306 is a radio transmitter, an ultrasound transmitter, a laser transmitter, another light source, or some combination thereof. The transmitter 306 transmits the signal through the tube 310 and any fluid 310 or bubble 320 within a monitoring region 330 of the tube 310 between the transmitter 306 and a corresponding receiver 307. The transmitter 306 is positioned along the outer surface 302 of the tube 301 between the proximal end surface 303 and the distal end surface 304. The transmitter transmits a signal 311 (e.g., an ultrasound signal), which travels across and through the tube 301 by entering the tube 301 via one side of the outer surface 302, traversing the intervening substance (e.g., the fluid 310 and/or one or more bubbles 320) within the monitoring region 330, and exiting an opposite side of the outer surface 302, where the receiver 307 is positioned. The outer surface 302 and the intervening substance (e.g., the fluid 310 and/or one or more bubbles 320) along the signal path attenuate the signal 311 (e.g., attenuate a speed or an intensity of the signal 311).

The receiver 307 is an electronic device that receives the attenuated signal 311 and outputs a detection signal that is correlated with the density of the substances within the monitoring region 330. The receiver 307 is positioned along the outer surface 302 of the tube 301 between the proximal end surface 303 and the distal end surface 304 on an opposite side of the monitoring region 330 as the receiver 306. The detection signal varies as a ratio of the fluid 310 to the second fluid (e.g., a ratio of the fluid 310 to a gas injected into the fluid 310) liquid to gas changes along the signal path as a result of the tube 301 changing its state. The detection signal can be used to determine the state of the tube 301. For example, the detection signal determines a geometric shape (e.g., an amount of bend) of the tube 301 that is indicative of an angular displacement of the body part (e.g., finger joint) contacting or proximate to the kinesthetic sensor 205. In some embodiments, the receiver 307 provides the detection signal to the kinesthetic sensing module 160 to determine an amount of bend in the kinesthetic sensor 205.

In some embodiments, the transmitter 306 and the receiver 307 each comprise a transceiver functioning as both a transmitter 306 and a receiver 307. Functions of a transceiver may change over time. For example, a transceiver alternates between acting as receiver or transmitter every unit of time (e.g., 100 microseconds). Additionally, in some embodiments, a single transmitter 306 may transmit to a plurality of receivers 307 (e.g., a transmitter 306 has 2 or more corresponding receivers 307). In a further embodiment, the fluid 310 and the second fluid are ferromagnetic. The state of the tube 301 is detected by measuring distribution of the bubbles as described herein. The state of the tube 301 may be further detected by measuring distribution of the magnetic field in the tube 301. A linear drive magnetic system is used to pump bubbles into the tube 301. Alternatively, the tube 301 includes only the fluid 310 that is ferromagnetic and the state of the tube 301 is detected by measuring distribution of the magnetic field in the tube 301.

Figure 3B:
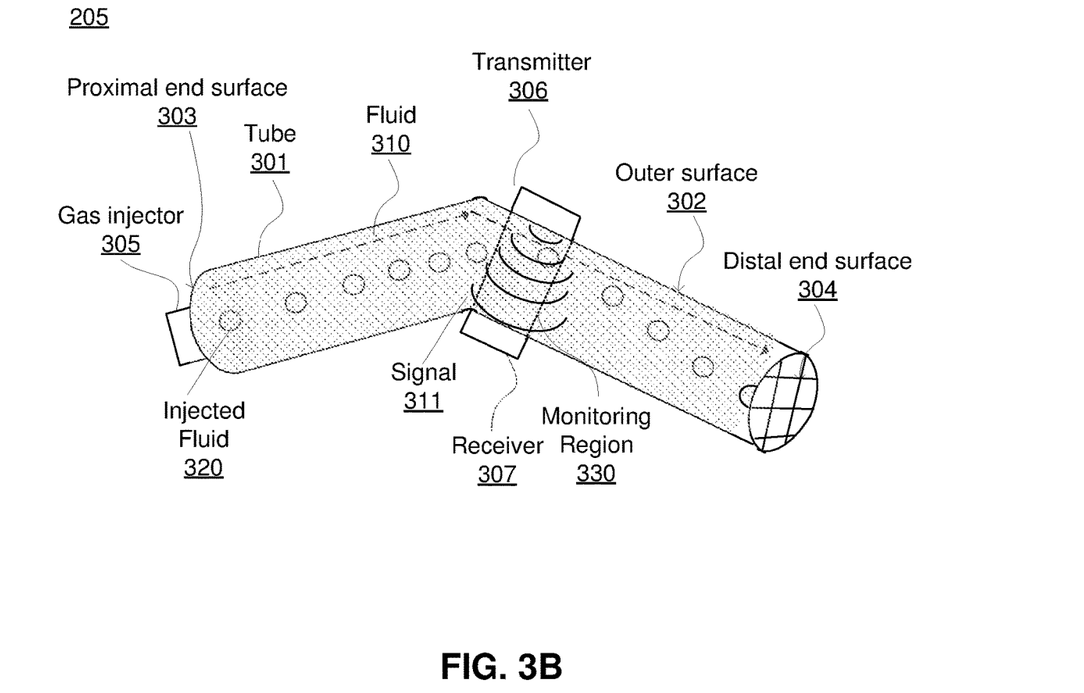
FIG. 3B illustrates the kinesthetic sensor of FIG. 3A in a bent state, in accordance with one embodiment.

FIG. 3B illustrates the kinesthetic sensor 205 of FIG. 3A in a bent state, in accordance with one embodiment. When the tube 301 is deformed from the straight state shown in FIG. 3A to the bent as illustrated in FIG. 3B, the bubbles 320 in the tube 301 are no longer evenly distributed in the tube 301. Hence, the distance between any two adjacent bubbles 320 may be different. The transmitter 306 transmits a signal 311 that travels across and through the tube 301 by entering the tube 301 via one side of the outer surface 302, traversing the intervening substance within the tube 301 (e.g., the fluid 310 and the second fluid), and exiting an opposite side of the outer surface 302, where the receiver 307 is positioned. Because the ratio of fluid 310 to the bubbles 320 changes in the monitoring region 330 as a result of the tube 301 changing its state, the receiver 307 receives an attenuated signal differing from the signal received when the tube 301 is in the straight state shown in FIG. 3A and outputs a detection signal comprising the distribution of volumes of the bubbles 320 of the second fluid along the signal path. Therefore, the detection signal can be used (e.g., by the kinesthetic sensing module 160) to determine a state (e.g., a geometric shape) of the tube 301 and/or the angular displacement of the corresponding body part contacting or proximate to the kinesthetic sensor 205.

In some embodiments, the injector 305 injects the second fluid at a temperature different from an ambient temperature. For example, the bubbles 320 may be at a higher temperature than an ambient temperature of a room including the kinesthetic sensor 205, and equalize temperature with the fluid 310 as the bubbles 320 propagate towards the distal end surface 304. Because of a temperature gradient (i.e., temperatures at different positions of the tube 301 are different) along the tube 301 from the different temperatures of the fluid 310 and the bubbles 320, pressure of the bubbles 320 vary across the tube 301. Hence, the temperature gradient along tube 310 may cause the bubbles 320 to change in dimension when traveling along the tube 310. This allows an absolute position of a bubble 320 to be determined based on a dimension of the bubble 320, as a bubble 320 has a unique dimension at a particular position of the tube 301.

Figure 4:
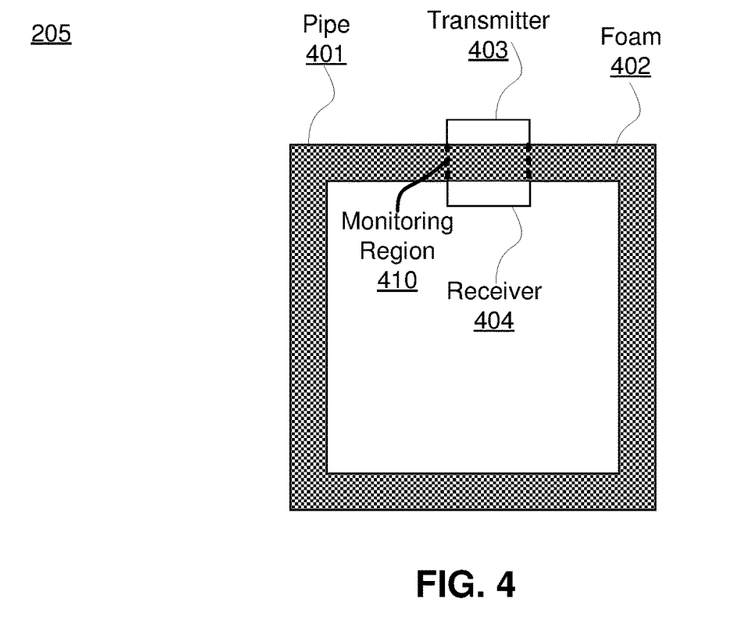
FIG. 4 illustrates a closed-loop kinesthetic sensor, in accordance with one embodiment.

FIG. 4 illustrates a closed-loop kinesthetic sensor 205, according to an embodiment. The kinesthetic sensor 205 includes a pipe 401, a transmitter 403, and a receiver 404. The transmitter 403 and the receiver 404 are similar to the transmitter 306 and the receiver 307 described above in connection with FIGS. 3A-B. The pipe 401 is closed-loop and contains a foam 402 including pockets of gas trapped in a liquid or in a solid. A closed loop pipe 401 does not have terminals where the foam 402 may enter or exit the pipe 401; thus, the foam 402 re-circulates within a closed-loop kinesthetic sensor 205. The pipe 401 may contain other substances having non-uniform consistency. Similar to FIGS. 3A and 3B, the transmitter 403 transmits a signal that travels through the pipe 401 and intervening foam 402 within a monitoring region 410 to the receiver 404. The receiver 404 receives an attenuated signal and outputs a detection signal correlated with the distribution of foam 402 within the monitoring region 410. Because the signal propagates at a different rate in air than through the liquid or the solid, the signal is attenuated and reflected at edges of bubbles in the foam 402. For example, the transmitter 403 emits sound waves that travel at a different speed in air than through the liquid, so the sound waves are attenuated and reflected at edges of the bubbles in the foam 402. A transmission efficiency and propagation time of the attenuated signal received by the receiver 404 may be used to determine the presence, volume, and density of the foam 402 in the monitoring region 410. Based on the received signal, the receiver 404 outputs a detection signal that may be used (e.g., by the kinesthetic sensing module 160) to determine a state of the kinesthetic sensor 205, such as a geometric shape of the pipe 401, or an angular displacement of the body part contacting or proximate to the kinesthetic sensor 205.

Figure 5:
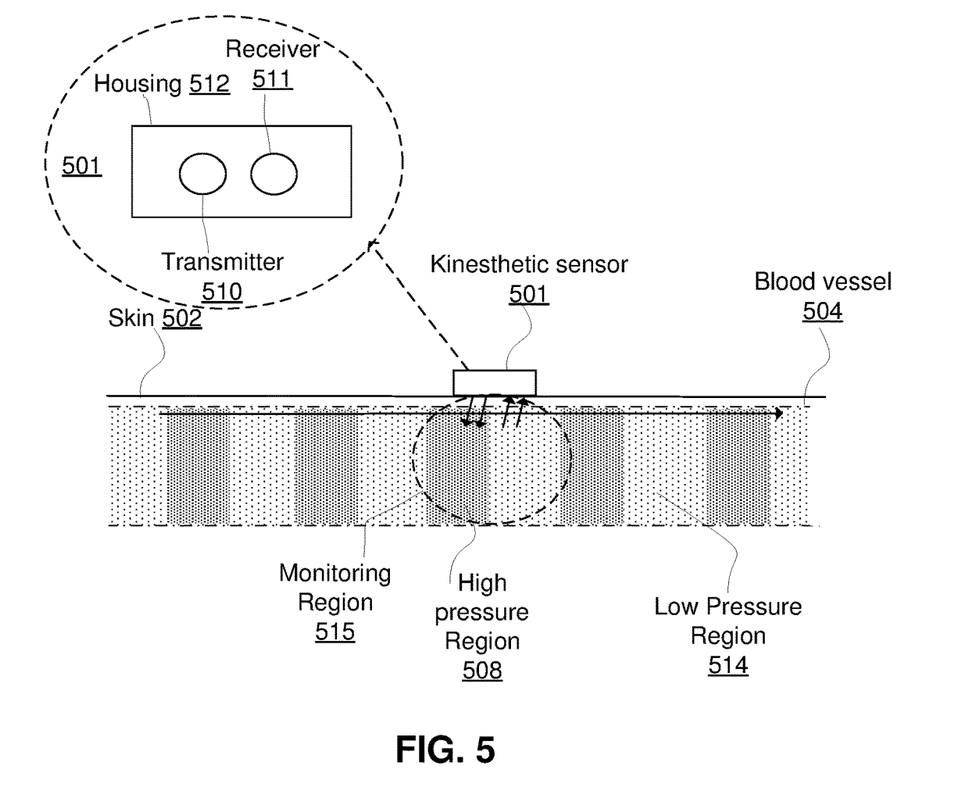
FIG. 5 illustrates a tubeless kinesthetic sensor in proximity to a blood vessel, in accordance with one embodiment.

FIG. 5 illustrates a tubeless kinesthetic sensor 501 in proximity to a blood vessel 504 of a user, according to an embodiment. The kinesthetic sensor 501 is placed over a body part (e.g., finger joint) of a user and includes a transmitter 510 and a receiver 511 affixed to a housing 512. The kinesthetic sensor 501 is positioned closely against a user's skin 502 and preferably positioned directly above a blood vessel 504. The transmitter 510 emits IR signals towards a monitoring region 515, which travels through the skin 502 and is reflected back to the receiver 512 by the user's blood. Some portion of the reflected signal is detected by the receiver 512, which outputs a detection signal. The user's heart pumping causes blood to propagate in the blood vessel 504. The propagating blood may be described by a series of high pressure regions 508 that are separated from each other by low pressure regions 410. The density of blood is higher in a high pressure region 508 than in a low pressure region 514. The high pressure region 508 and the low pressure region 514 reflect different amounts of the IR signal emitted by the transmitter 510. The receiver 511 measures the reflected IR signals and outputs a detection signal representing the blood density within the monitoring region 515 of the blood vessel 504. The blood vessel 504 is akin to the tube 301 described above with reference to FIGS. 3A and 3B. Because the blood pulses propagate through the blood vessel 504, the detection signal may be used (e.g., by the kinesthetic sensing module 160) to determine a change in the density profile of blood within the monitoring region 515 of the blood vessel 504, which is indicative of a state of the angular displacement of the body part over which the kinesthetic sensor 501 was placed.

Additionally, in some embodiments, propagation of blood pulses over time can be measured by a series of kinesthetic sensors 501 that are proximate to different locations along the blood vessel 504. In alternate embodiments, the transmitter 510 and receiver 511 are components of a single transceiver. The transceiver may transmit and receive IR signals simultaneously. Alternatively, as further described above in conjunction with FIGS. 3A and 3B, the transceiver may alternate between functioning as a transmitter 510 or as a receiver 511 at different time intervals. In further embodiments, propagation of blood pulses over time can be measured by measuring distribution of magnetic field.

Additional Configuration Information

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method comprising:
   maintaining a density profile, the density profile including data associating each of a plurality of detection signals with a corresponding density and a corresponding angular displacement from a reference state;
   receiving, at a console, a detection signal from a kinesthetic sensor, the detection signal based on a density of a portion of a substance included in a conduit of the kinesthetic sensor, the substance having a non-uniform consistency, and wherein the kinesthetic sensor includes a transmitter configured to transmit a signal through the portion of the substance included in the conduit and a receiver configured to receive the signal and to generate the detection signal;
   identifying an angular displacement corresponding to the received detection signal from the density profile; and
   generating feedback for communication to a user based on the identified angular displacement.

2. The method of claim 1, wherein maintaining the density profile comprises:
   receiving training data including a set of angular displacements of the conduit of the kinesthetic sensor labeled with signal characteristics;
   developing one or more machine learning models correlating angular displacements from the reference state with characteristics of the detection signal; and
   storing the one or more machine learning models.

3. The method of claim 1, wherein identifying an angular displacement comprises:
   providing the detection signal to a machine learning model, the machine learning model correlating angular displacements from the reference state with characteristics of the detection signal,
   wherein the machine learning model is configured to output the angular displacements.

4. The method of claim 1, wherein identifying the angular displacement corresponding to the received detection signal from the density profile comprises:
   receiving detection signals from the kinesthetic sensor when a user associated with the kinesthetic sensor performs a predetermined motion of a body part proximate to the kinesthetic sensor;
   determining correlations between changes in density within the conduit of the kinesthetic sensor and angular positions of the kinesthetic sensor while the user performs the predetermined motion from the received detection signals; and
   storing the determined correlations as the density profile.

5. The method of claim 1, wherein the density profile includes correlations between changes in density within the conduit of the kinesthetic sensor and angular positions of the kinesthetic sensor, and wherein identifying an angular displacement includes determining which angular position is correlated with a density corresponding to the detection signal.

6. The method of claim 1, wherein the conduit is flexible and has an outer surface and the transmitter is positioned proximate to a side of the outer surface of the conduit and configured to transmit the signal through the conduit towards an opposite side of the outer surface that is parallel to the side of the outer surface, and wherein the receiver is positioned on a side of the opposite side of the outer surface and configured to receive the signal after the signal propagates from the side of the outer surface through a portion of the substance included in the conduit between the transmitter and receiver.

7. The method of claim 6, wherein the substance is a foam comprising a liquid and pockets of gas separated by the liquid.

8. The method of claim 6, wherein the substance is a foam comprising a solid and pockets of gas separated by the solid.

9. The method of claim 6, wherein the density of the portion of the substance included in the conduit between the transmitter and the receiver corresponds to an angular displacement of the kinesthetic sensor.

10. The method of claim 1, wherein the transmitter is positioned proximate to a portion of a user's body including a blood vessel and configured to transmit the signal and the receiver is positioned proximate to the portion of the user's body including the blood vessel and configured to receive the signal reflected from a portion of the blood vessel proximate to the transmitter, and wherein the detection signal indicates a density of blood within the portion of the blood vessel proximate to the transmitter based on the received signal.

11. The method of claim 10, wherein the kinesthetic sensor further comprises a housing including the transmitter and the receiver, the housing configured to be placed over the portion of the user's body including the blood vessel.

12. The method of claim 10, wherein the density of blood within the portion of the blood vessel proximate to the transmitter corresponds to an angular displacement of the portion of the user's body.

13. A system comprising:
   a processor; and
   non-transitory memory storing computer instructions configured to cause the processor to perform:
      maintaining a density profile, the density profile including data associating each of a plurality of detection signals with a corresponding density and a corresponding angular displacement from a reference state;
      receiving, at a console, a detection signal from a kinesthetic sensor, the detection signal based on a density of a portion of a substance included in a conduit of the kinesthetic sensor, the substance having a non-uniform consistency, and wherein the kinesthetic sensor includes a transmitter configured to transmit a signal through the portion of the substance included in the conduit and a receiver configured to receive the signal and to generate the detection signal;

identifying an angular displacement corresponding to the received detection signal from the density profile; and generating feedback for communication to a user based on the identified angular displacement.

14. The system of claim 13, wherein maintaining the density profile comprises:

receiving training data including a set of angular displacements of the conduit of the kinesthetic sensor labeled with signal characteristics;

developing one or more machine learning models correlating angular displacements from the reference state with characteristics of the detection signal; and storing the one or more machine learning models.

15. The system of claim 13, wherein identifying an angular displacement comprises:

providing the detection signal to a machine learning model, the machine learning model correlating angular displacements from the reference state with characteristics of the detection signal, wherein the machine learning model is configured to output the angular displacements.

16. The system of claim 13, wherein identifying the angular displacement corresponding to the received detection signal from the density profile comprises:

receiving detection signals from the kinesthetic sensor when a user associated with the kinesthetic sensor performs a predetermined motion of a body part proximate to the kinesthetic sensor;

determining correlations between changes in density within the conduit of the kinesthetic sensor and angular positions of the kinesthetic sensor while the user performs the predetermined motion from the received detection signals; and storing the determined correlations as the density profile.

17. The system of claim 13, wherein the density profile includes correlations between changes in density within the conduit of the kinesthetic sensor and angular positions of the kinesthetic sensor, and wherein identifying an angular displacement includes determining which angular position is correlated with a density corresponding to the detection signal.

18. A non-transitory computer storage medium storing instructions configured to be processed by a computer processor to cause the computer processor to perform:

maintaining a density profile, the density profile including data associating each of a plurality of detection signals with a corresponding density and a corresponding angular displacement from a reference state;

receiving, at a console, a detection signal from a kinesthetic sensor, the detection signal based on a density of a portion of a substance included in a conduit of the kinesthetic sensor, the substance having a non-uniform consistency, and wherein the kinesthetic sensor includes a transmitter configured to transmit a signal through the portion of the substance included in the conduit and a receiver configured to receive the signal and to generate the detection signal;

identifying an angular displacement corresponding to the received detection signal from the density profile; and generating feedback for communication to a user based on the identified angular displacement.

19. The non-transitory computer storage medium of claim 18, wherein maintaining the density profile comprises:

receiving training data including a set of angular displacements of the conduit of the kinesthetic sensor labeled with signal characteristics;

developing one or more machine learning models correlating angular displacements from the reference state with characteristics of the detection signal; and storing the one or more machine learning models.

20. The non-transitory computer storage medium of claim 18, wherein identifying the angular displacement corresponding to the received detection signal from the density profile comprises:

receiving detection signals from the kinesthetic sensor when a user associated with the kinesthetic sensor performs a predetermined motion of a body part proximate to the kinesthetic sensor;

determining correlations between changes in density within the conduit of the kinesthetic sensor and angular positions of the kinesthetic sensor while the user performs the predetermined motion from the received detection signals; and storing the determined correlations as the density profile.

* * * * *